United States Patent
Kneissl et al.

(10) Patent No.: US 9,498,550 B2
(45) Date of Patent: Nov. 22, 2016

(54) FLOW CYTOMETER DISINFECTION MODULE

(75) Inventors: Michael Kneissl, Berlin (DE); Toralf Kaiser, Birkenwerder (DE); Tim Kolbe, Berlin (DE)

(73) Assignees: DEUTSCHES RHEUMA-FORSCHUNGSZENTRUM BERLIN, Berlin (DE); TECHNISCHE UNIVERSITÄT BERLIN, Berlin (DE)

( * ) Notice: Subject to any disclaimer, the term of this patent is extended or adjusted under 35 U.S.C. 154(b) by 403 days.

(21) Appl. No.: 14/004,394

(22) PCT Filed: Mar. 12, 2012

(86) PCT No.: PCT/EP2012/054273
§ 371 (c)(1),
(2), (4) Date: Oct. 31, 2013

(87) PCT Pub. No.: WO2012/123412
PCT Pub. Date: Sep. 20, 2012

(65) Prior Publication Data
US 2014/0050612 A1   Feb. 20, 2014

Related U.S. Application Data

(60) Provisional application No. 61/451,796, filed on Mar. 11, 2011.

(51) Int. Cl.
*A61L 2/10*   (2006.01)
*G01N 15/14*   (2006.01)

(52) U.S. Cl.
CPC ............. *A61L 2/10* (2013.01); *G01N 15/1404* (2013.01); *G01N 2015/149* (2013.01); *G01N 2015/1409* (2013.01)

(58) Field of Classification Search
CPC ............................. A61L 2/10; G01N 15/1404
USPC .......................................... 422/124; 250/435
See application file for complete search history.

(56) References Cited

U.S. PATENT DOCUMENTS

| 5,366,705 A * | 11/1994 | Reidy ..................... A61L 2/10 210/243 |
| 2002/0118362 A1 * | 8/2002 | Saccomanno ...... G01N 15/1456 356/246 |
| 2009/0250626 A1 * | 10/2009 | Schlesser ............... A61L 2/0011 250/455.11 |
| 2009/0294688 A1 * | 12/2009 | Evans ....................... A23L 3/28 250/436 |

FOREIGN PATENT DOCUMENTS

| WO | WO 01/96340 A1 | 12/2001 |
| WO | WO 2008/019448 A1 | 2/2008 |
| WO | WO 2010/001254 A2 | 1/2010 |

* cited by examiner

*Primary Examiner* — Sean E Conley
(74) *Attorney, Agent, or Firm* — Knobbe, Martens, Olson & Bear, LLP

(57) ABSTRACT

A flow cytometer disinfection module is useful for disinfecting a sheath fluid in a flow cytometer. The module includes a flow cell and at least one UV-C and/or UV-B light source. The UV-C and/or UV-B light source is disposed about the cell and irradiates a sheath fluid passing through the cell.

23 Claims, 9 Drawing Sheets

A

B

A

B

FLOW CYTOMETER DISINFECTION MODULE

Figure 1A:
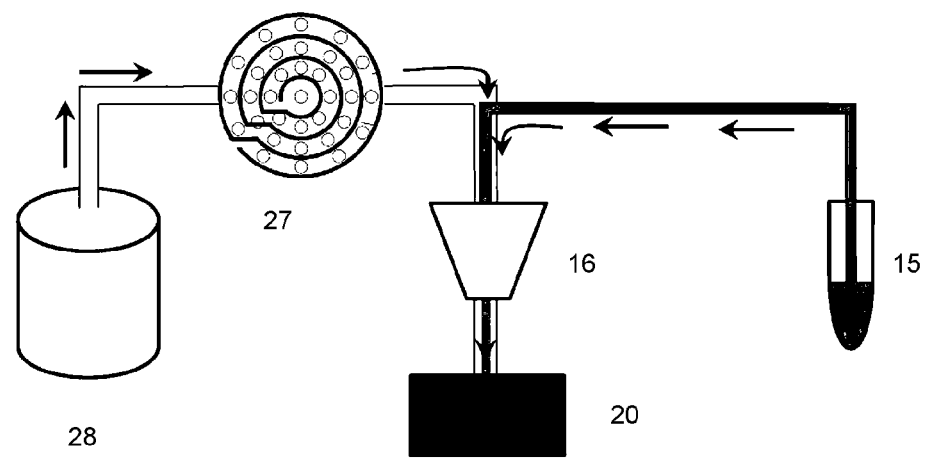

The invention concerns a flow cytometer disinfection module for disinfecting a sheath fluid in a flow cytometer, comprising a flow cell and at least one preferably UV-C and/or UV-B light source. The preferably UV-C and/or UV-B light sources are disposed about the flow cell and irradiate the sheath fluid flowing through the cell. The invention also concerns a method for disinfecting a sheath fluid in a flow cytometer.

BACKGROUND

Generally, cell sorting devices separate cell populations of interest from a suspension and/or other types of cells. The principal method of Operation of early cell sorting devices relied on a cell's physical parameters to distinguish that cell from a suspension and/or other types of cells. Examples of bulk cell sorting techniques include filtration, which is based on cell size, and centrifugation, which is based on cell density. These techniques are effective as long as the cell population of interest is significantly different, with respect to size or density, from the suspension and/or the other cells in the population (i.e. a separation of red blood cells from blood). However, when the cell population of interest does not differ significantly in size or density, the filtration and centrifugation techniques are ineffectual.

In attempting to address this problem, a technique was developed which did not rely on cell size or density differences relative to the suspension and/or the other cells in the population. This technique was based on the presence of a tagging element, which was attached to the surface of the cell. This tagging technique has evolved to become a significant analytical tool in basic biological studies, applied biological studies, in the clinical diagnosis of diseases and the rapidly developing cell-based therapies in the treatment of diseases.

One application of this tagging technique is known as Fluorescence-Activated Cell Sorting (hereinafter FACS). In the FACS technique, an antibody-fluorescent label conjugate is used to tag a specific cell surface marker. The primary mode of Operation of a FACS sorter is binary in nature, that is, it determines whether a cell has the threshold number of fluorescent labels (i.e. positive sorting) or it does not have the threshold number of fluorescent labels (i.e. negative sorting). This determination is made by passing cells, single file, through a device which can determine whether each cell includes the parameter of interest (e.g. fluorescence). The binary separation is determined by the setting of a threshold or "gate" (also sometimes called a trigger). While the value of this "gate" or trigger is adjustable (i.e. quantitatively), the sorting process is still binary based on the threshold setting.

Furthermore, the rate of cell separation is relatively slow due to the fact that FACS sorters operate by examining a single cell at a time. Generally, a FACS sorter can provide a cell sorting rate of up to 30.000 cells/second. Higher cell sorting rates are possible, however, these higher sorting rates may decrease the yield. Still further, FACS sorters are relatively expensive and thus, most laboratory facilities are equipped with a limited number of sorters.

Another technique employing cell tagging as a basis for separation is known as High Gradient Magnetic Separation (hereinafter HGMS). The concept of sorting materials based on their magnetic responsiveness was first introduced in the industrial and mining arts. These methods relied on the intrinsic magnetic properties of the sorted material (generally, iron (i.e. magnetic) from non-iron parts (i.e. non-magnetic)) as a basis of Operation.

More particularly, in HGMS, a heterogeneous cell population, which includes a cell sub-population having magnetic cell tags, is passed through a magnetic field. As the heterogeneous cell population passes through the magnetic field, the cell sub-population labeled with the magnetic cell tags, becomes magnetically responsive to the applied magnetic field. That is, the cell sub-population including the magnetic tags will be subjected to a magnetic force which will cause the cells to be either attracted to (in the typical case), or repelled from, the magnetic field's source. Typically, the cell sub-population having the magnetic tags is attracted to the source of the magnetic field and collected by adhering to the magnetic source itself, or adhering to a cell collector device situated near the magnetic source. Therefore, the primary mode of the HGMS is also binary in nature, that is, it determines whether a cell has the magnetic tags or not.

The HGMS system, however, also has several drawbacks. Firstly, the cell sub-population of interest can be physically damaged during the HGMS process because of their forced magnetic massing at the collector device. Secondly, because the HGMS process sorts cells on the same fundamental principle as the FACS system, the HGMS method is also binary in nature. That is, both the FACS and HGMS systems separate cells based on the presence or absence of a parameter of interest (i.e. fluorescence and magnetic responsiveness, respectively).

Conventional flow cell sorters, such as FACS, are designed to have a nozzle with or without a flow chamber and use the principle of hydrodynamic focusing with sheath flow to separate or sort biological material such as cells. In addition, most sorting instruments combine the technology of ink-jet writing and the effect of gravity to achieve a high sorting rate of droplet generation and electrical charging. Despite these advances, many failures of these instruments are due to problems in the flow chamber or the nozzle. For example, orifice clogging, particle adsorption and contamination in the tubing may cause turbulent flow in the jet stream. These problems contribute to the great variation in illumination and detection in conventional FACS devices. Another major problem is known as sample carryover, which occurs when remnants of previous specimens left in the channel back-flush into the new sample stream during consecutive runs. Although such systems can be sterilized between runs, it is costly, time consuming, inefficient, and results in hours of machine down time for bleaching and sterilization procedures.

Sterile cell sorting is one of the biggest challenges in flow cytometry. Usually cell sorter are not in a sterile environment and therefore the risk of contaminations exists. The ability to prepare a cell sorter for aseptic sorting is essential. Standard protocols for performing a sterile sort are based on washing procedures by using Ethanol or other sterilizing reagents and should be performed in a time-consuming daily routine. However, these reagents are expensive and some are toxic for cells if they are not completely washed.

It is described in the state of the art, that ultraviolet systems can be used for water disinfection.

Ultraviolet light is a technology used in the drinking water treatment industry for disinfection of microorganisms in water. Recently, antimicrobial devices such as UV toothbrush sanitizers and UV disinfection wands have been disclosed. As with chemical disinfectants, the extent of disinfection that comes about from UV treatment is a function of both the duration and intensity of treatment. Ultraviolet (UV) radiation or light is defined as that portion of the electromagnetic spectrum between x rays and visible light, i.e., between 40 and 400 nm. The UV spectrum is divided into Vacuum UV (40-190 nm), Far UV (190-200 nm), UV-C (200-280 nm), UV-B (280-320), and UV-A (320-400 nm). Artificial sources of UV radiation include high, medium, and low pressure mercury vapor lamps, halogen lights, high-intensity discharge lamps, deuterium lamps, fluorescent and incandescent sources, and some types of lasers (excimer lasers, nitrogen lasers, and third harmonic Nd:YAG lasers). UV-C is almost never observed in nature because it is absorbed completely in the atmosphere, as are Far UV and Vacuum UV. Germicidal lamps are designed to emit UV-C radiation because of its ability to kill bacteria, viruses, molds, and spores or at least to prevent their reproduction. UV-B is typically the most destructive form of UV radiation because it has enough energy to cause photochemical damage to cellular DNA, yet not enough to be completely absorbed by the atmosphere. UV-A is the most commonly encountered type of UV light. Most phototherapy and tanning booths use UV-A lamps.

Ultraviolet radiation is used to kill microorganisms, molds and fungus in various environmental applications. UV sterilization is used for air-purification systems, water purification, aquarium and pond maintenance, laboratory hygiene and food and beverage protection.

UV treatment generally takes place only inside a specialized UV exposure chamber. It is useful for targeted elimination of microorganisms in air and water. UV sterilization leaves no residual chemical or radiation in the air or water and is harmless to untargeted animals and plants. UV works well with waterborne pathogens. Water should be filtered prior to UV exposure to improve penetration and the sterilization effect. Sterilized microorganisms remain in the air or water.

Germicidal ultraviolet radiation is primarily intended for the destruction of bacteria and other microorganisms in the air or on exposed surfaces. Ultraviolet light kills microorganisms by damaging the DNA. UV radiation disrupts the chemical bonds that hold the atoms of DNA together in the microorganism. If the damage is severe enough, the bacteria cannot repair the damage and will die. Longer exposure to UV light is necessary to ensure complete kill-off of all microorganisms. Unlike chemical treatments, UV-treated air or water does not resist re-contamination. In order for ultraviolet light to kill bacteria, the rays must directly strike the microorganism. Microorganisms floating in the air or on an outer surface may easily be reached by the ultraviolet rays and, therefore, are readily destroyed. If however, the microorganisms are hidden below the surfaces of a material or are not in the direct path of the rays, they will not be destroyed.

The exposure to ultraviolet necessary to kill bacteria is the product of time and intensity. High intensities for a short period of time, or low intensities for a long period are fundamentally equal in lethal action on bacteria disregarding the life cycle of the bacteria.

SUMMARY OF THE INVENTION

It was an objective of the invention to provide a device and a method for disinfection of the sheath fluid in a flow cytometer.

This problem is solved by the features of the independent claims. Preferred embodiments of the present invention are provided by the dependent claims.

The various aspects of the present invention, such as the device, method and use of the device described herein, represent a unified invention, as all are defined by novel and inventive features in light of the cited prior art. It was at the date of filing unknown, that preferably UV-C and/or UV-B light can be used for disinfection in a flow cytometer, especially without the need to replace the cytometer. The novel and inventive module can easily be attached to existing cytometer.

In a first aspect, the invention concerns a flow cytometer disinfection module, comprising a flow cell and at least one preferably UV-C and/or UV-B light source, wherein the at least one preferably UV-C and/or UV-B light source is disposed about the cell and irradiates a sheath fluid passing through the cell. It was very surprising, that a preferably UV-C and/or UV-B light source, especially a UV-C semiconductor or a UV-C LED can be used to disinfect the sheath fluid in a cytometer, wherein at least one light source is disposed about the cell through which the sheath fluid is flowing. The preferably UV-C and/or UV-B light is irradiating the sheath fluid, thereby damaging possible microorganisms in the fluid irreparably. This embodiment not only realises saving of time, but also of material, work steps and costs. The use of an UV light source based disinfection module in flow cytometer, especially in cell sorting machines results in a significant reduction in preparation time before the sorting or analysis of the cells because a flushing of the tubing of the cytometer is not necessary anymore. In addition, the incorporation of the module in a flow cytometer is an additional safety step to ensure the work with not contaminated carrier liquids. The quality of the sorting or the analysis of the cells increases significantly.

The flow cell of the module preferably comprises an interior and an outer region and inlet and outlet ports, through which the sheath fluid is flowing, wherein the flow cell is configured to communicate a fluid from the one or more inlet ports to the one or more outlet portions through an interior portion thereof.

In a preferred embodiment, the flow cytometer disinfection module is characterized in that the module is connected to the sheath fluid tubing and installed between a nozzle and a sheath fluid tank of the cytometer.

Furthermore, it is preferred that the cell is linear, spiral, U-shaped, cylindrical, rectangular, helical or ellipsoid shaped.

In a preferred embodiment the cell comprises inlet and outlets ports. Also preferred is that the cell is made out of PTFE.

Furthermore, it is preferred that the light source is a LED or a semiconductor. In another preferred embodiment the module as described herein is characterized in that the cell is made of polymer, glass and/or metal.

It is also preferred, that the cell comprises mechanical baffles and/or stirring mechanisms disposed within the cell.

In a preferred embodiment the cell comprises an interior surface for reflecting the radiation. It is preferred that the cell comprises at least one sensor.

A flow cytometer disinfection module is preferred, wherein a cooling device is mounted to the cell.

The light source is preferably assembled within a wall of an interior region of the cell. In another preferred embodiment, the preferably UV-C and/or UV-B light source is assembled in a light-permissive housing within a wall of the interior region of the cell or is arranged outside the interior region of the cell irradiating the sheath fluid through a light-permissive material.

The at least one preferably UV-C and/or UV-B LED emits preferably light with 265 nm (+/−25 nm) and/or is preferably is gallium nitride based.

The cell of the flow cytometer disinfection module comprises preferably a control electronic for activating and deactivation of the light source. It is furthermore preferred, that more than 5, especially more than 10 preferably UV-C and/or UV-B light sources are disposed within the cell.

The preferably UV-C and/or UV-B light sources are preferably divided into groups that are activated separately by the control electronic. In a preferred embodiment, the preferably UV-C and/or UV-B light sources are operated intermittently, continuously or quasi-continuously (i.e. pulsed with very high duty cycle).

In another preferred embodiment, a focussing or diffusing optic is arranged in front of the light sources. The preferably UV-C and/or UV-B light source of the flow cytometer disinfection module is preferably operated with an accumulator or batteries.

The invention also concerns a method for disinfecting a sheath fluid in a flow cytometer, said method comprising the steps of:
- installing a flow cytometer disinfection module between a nozzle and a sheath fluid tank, wherein the sheath fluid is pumped through the cell;
- providing at least one preferably UV-C and/or UV-B light source, and
- irradiating the sheath fluid passing through the cell with the light source,
- wherein the light source is arranged within or outside of the cell.

In another aspect, the invention concerns a use of the flow cytometer disinfection module for flow-through disinfection in a flow cytometer, wherein a sheath fluid is flowing through the module and is irradiated by at least one light source.

DETAILED DESCRIPTION OF THE INVENTION

Various methods are described in the state of art, which apply chemical disinfection procedures to a flow cytometer. However, these procedures not only damage the tubing but are also cost intensive and time consuming. In addition, antibiotics, antimycotic, antiprotozoal or antiviral compositions are added to the analyzed cell solution to prevent contaminations. These drugs have various side effects and also influence cell growth. It was very surprising, that by applying the module to a flow cytometer, the usage of drugs or chemicals can be minimized or even abandoned. The sheath fluid is disinfected by applying irradiation deriving from at least one preferably UV-C and/or UV-B light source, preferably a semiconductor or a light emitting diode (LED). The LED can be realized as a single light source, in a group or in an array, such as a LED array. Therefore, multiple LED, especially UV LED arrays can be used to disinfect the sheath fluid. The light source can be arranged in various ways within or outside of the flow cell, wherein the sheath fluid is irradiated from the outside and/or inside of the cell. The sheath fluid can be irradiated from above, below and/or from the sides.

The term "flow cytometer" is known to the person skilled in the art and comprises all cytometers that can be used for cell sorting and cell analysis. Therefore, the module can be used in flow cytometers for cell sorting or cell analysis and also for HG MS.

In the sense of the invention, a sheath fluid has preferably the same salinity of the analyzed sample. For fresh water samples, PBS (phosphate buffered saline) or milliQ distilled deionised water is used. The sheath fluid preferably carries and aligns the cells to be analyzed so that they pass single file through the light beam of the cytometer.

In the sense of the invention, the term "disinfection" describes a process which ultimately results in a destruction or irreparable damage of microorganisms in the sheath fluid. The term also applies to damaging a biological substance, fluorescent label and fluorochrome. It was surprising, that the module can also be used to bleach fluorophores attached to antibodies, that are used for labelling and analyzing cells.

The terms "fluorescent label" or "fluorophore" refer to compounds that comprise a fluorochrome (or fluorescent chromophore) covalently bonded to a macromolecule and used to stain cells. The fluorophore absorbs light energy of a specific wavelength and re-emits energy at a longer wavelength. The wavelength, amount, and time before emission of the emitted energy depend on both the fluorophore and its chemical environment as the molecule in its excited state interacts with surrounding molecules. Fluorescein isothiocyanate (FITC), a reactive derivative of fluorescein, is one of the most common fluorophores chemically attached to other, non-fluorescent molecules to create new fluorescent molecules. Other common fluorophores are derivatives of rhodamine, coumarin, naphthalene, cyanine, oxadiazole, pyrene, oxazine, acridine, arylmethine and tetrapyrrole. The module can easily be attached to a flow cytometer performing fluorescence-activated cell sorting (FACS). It was very surprising, that the module can be installed between the nozzle and the sheath fluid tank of the cytometer in order to disinfect the sheath fluid. This way, it can also be integrated into already installed cytometers, without the need of further modifications.

To disinfect the sheath fluid flowing through the cell, at least one, preferably five and especially preferred 10 or more preferably UV-C and/or UV-B light sources are arranged within the interior portion and/or outside the cell. The sheath fluid is being pumped through the interior region of the cell, wherein it commutes between the inlet and outlet ports.

In a preferred embodiment, semiconductor based light emitters are used to irradiate the sheath fluid, preferably semiconductor based LEDs. A semiconductor is preferably a material with electrical conductivity intermediate between that of a conductor and an insulator. Semiconductor light emitters include light-emitting diodes (LEDs), laser diodes (LDs), vertical surface emitting laser diodes (VCSELs), and superluminescent LEDs. Preferred semiconducting materials are crystalline solids, but polycrystalline and amorphous semiconductors are also preferred. These include gallium nitride, aluminium nitride, indium nitride, boron nitride and their alloys in a variety of proportions. Such compounds share with better known semiconductors intermediate conductivity and a rapid variation of conductivity with temperature. Other semiconductors may include ZnO, MgO, CdO, BeSe, MgS, ZnS, and their alloys as well as diamond. Organic semiconductors are also preferred, that is, organic materials with properties resembling conventional semiconductors.

The preferred light sources are a mercury free solid state light source. In addition to being mercury free, the light sources have some distinct advantages over lamp sources. Lamps are bulky and require line voltage which is undesirable in flow cytometer, where line voltage is not always available where the module would be positioned. Furthermore, the module can be used with batteries or accumulators, allowing to attach the module to already installed flow cytometers without the need for additional modifications. Also, mercury lamps have a start-up delay time associated with the creation of the plasma in the lamp envelop, which in turn heats the inert gas, which then vaporizes the mercury allowing the mercury and plasma ions to collide and excite the Hg to emission. In contrast, semiconductor light sources, especially UV-C and/or UV-B LEDs may be turned on and off instantly and operated at a very fast on/off duty cycle to increase their lifetime and also allow advanced UV disinfection protocols including short high power UV light pulses. In the sense of the invention, the term "instantly" describes especially on- and off-switching time in the range from nano-seconds to micro-seconds.

The module uses in a preferred embodiment compact UV-C and/or UV-B LEDs to sterilize the sheath fluid at the point of use. In a preferred embodiment, gallium nitride UV-LEDs are used. Gallium nitride (GaN) based preferably UV-C and/or UV-B LEDs have attracted increasing interest as novel preferably UV-C and/or UV-B radiation sources for applications in water purification and disinfection. However, their use in flow cytometry has not been exploited. Their innovative potential is based on significant advantages compared to conventional gas-discharge lamps.

It was very surprising, that irradiation with light sources, especially UV-C LEDs disinfects the sheath fluid very efficiently. DNA has peak absorption at about 260 nm, but the absorption curve is broad, with the majority of UV absorption occurring between about 240 nm and about 290 nm. Low and medium pressure mercury lamps have emission peaks at about 253.7 nm, with medium pressure lamps having emission peaks which are narrow and sporadic across the peak microbicidal region of DNA. In comparison, UV-LEDs have broadband deep-UV emission and UV-C LEDs are tailored for peak emission at about 265 nm to provide the maximum dose more effectively than mercury lamps. In the UV-C spectral region, with a local maximum at about 265 nm, the germicidal potential of UV-radiation is known to be most effective due to the absorption spectrum of DNA. In previous studies it was demonstrated that LEDs with emission wavelength at 269 nm are more effective in inactivating micro-organisms than conventional mercury lamps emitting at 254 nm. It was also surprising that 282 nm LED are overall better suited to disinfect larger volumes of liquids due to the nearly two-times higher output power of these LEDs.

In addition, the preferred light sources contain no mercury, which is extremely toxic such that discharge lamps containing mercury must be treated as hazardous waste and sent to an approved recycling facility when spent. Also, mercury based sources produce emission lines at about 185 nm, which results in ozone production; ozone is corrosive and absorbs UV light, as well as being toxic.

Furthermore, the preferred light sources, especially UV-C and/or UV-B LEDs yield compact form factors, operate at very low dc voltages, exhibit fast on/off switching capabilities and their emission wavelength can be tailored to the optimum wavelength for germicidal effectiveness.

The flow cell is preferably made of metal, polymer or glass. Accordingly, it can be manufactured in a preferred embodiment of stainless steel, aluminium but also of other metals. Metals indicate those chemical elements that, in contrast to the non-metals, are found in the periodic table to the left of the diagonal dividing line starting with the element beryllium (2nd group) through polonium (16th group), with their alloys and intermetallic compounds (including Laves phases, Heusler phases, Zintl phases, Hume-Rothery phases, NiTi, Co5, Nb3Sn and Ni3Al) with characteristic metallic properties. Metals include aluminum, beryllium, bismuth, lead, cadmium, chromium, iron, gallium, gold, indium, potassium, cobalt, copper, magnesium, manganese, molybdenum, sodium, nickel, osmium, palladium, platinum, rhodium, ruthenium, silver, tantalum, titanium, vanadium, tungsten, zinc and tin.

Alternatively, one can also use polymeric materials from which the cell can be formed. Polymers are taken to mean, pursuant to the definition of IUPAC ("The International Union of Pure and Applied Chemistry"), substances that are composed of a collective of chemical macromolecules (polymer molecules), which as a rule differ in terms of polymerization, molecular weight and chain length. In such so-called single polymer materials, so all macromolecules have the same structure and differ only in their chain length (polymerization). Such polymers can be described as a polymer homologue. Polymers can be selected from the group that consists of inorganic polymers, organometallic polymers, fully or partially aromatic polymers, homopolymers, copolymers, biopolymers, chemically modified polymers and/or synthetic polymers, and include polyethylene, polypropylene, polyvinyl chloride, polystyrene, polymethylmethacrylate, polyimide, polyester, polycarbonate, polyethylene terephthalate, polyethylene glycol, dendrimers, silicones, proteins, DNA, RNA, carbohydrates, polyether ether ketone (PEEK) and polyhydroxxyalkanoate. Preferentially, polytetrafluoroethylene (PTFE) is used. Highly UV-reflective PTFE materials are sold under the brand name Spectralon by Labsphere Inc. and under the brand name ePTFE by W. L. Gore & Associates, Inc. The UV reflectance of these PTFE materials is typically larger than 95%. PTFE materials are also inert to almost all known chemicals which are beneficial to prevent any interaction between the liquid and the module. Moreover, these materials have a low contact angle for water which will help to prevent air bubbles and also allows a laminar flow inside the module.

Furthermore, the flow cell can be made of glass, preferably a light-permissive glass. In a preferred embodiment, the sheath fluid is flowing through cell at least partly made of glass, wherein the preferably UV-C and/or UV-B light sources are arranged outside the glass part of the cell.

The interior surface of the interior region of the cell is operable for reflecting the radiation delivered to the sheath fluid by the one or more preferably UV-C and/or UV-B light sources such that a radiation intensity is preferably uniform throughout the interior portion of the flow cell. The material of the cell is preferably highly reflecting or coated with metal, organic polymer, silicone, inorganic oxide, or anodized material. Using a reflecting coating, an uniformly distributed radiation inside the interior of the cell can be assured. The coating can for example be realized by applying MgO, ZrO2, BaSO4 or SiO2 to the surface of the cell. As an enhancement to the disinfection efficiency of the module, photocatalytic materials, such as titanium dioxide (TiO2), zinc oxide, zirconium dioxide, iron oxide, aluminum oxide, Fe(III)/Al2O3, cerium oxide, manganese oxide, titanium silicates, metal substituted silicates or aluminosilicates, and any other metal oxide, mixed metal oxide, and/or metal doped/supported metal oxide substrates (e.g. gold nanoparticles supported on silicon dioxide or titanium dioxide), or the like, may also be included inside the cell or as part of the internal surface of the cell to enhance photo-oxidation, photo-reduction, and the decontamination of sheath fluid.

In order to increase the residence time for every micro-organism in the cell, it is anticipated that the flow of the sheath fluid should be disrupted somewhere in the cell, to slow down the relatively fast moving polar axial jet, and to sweep clean the relatively stagnant equatorial volume. This can be achieved by applying mechanical baffles and/or stirring mechanisms to the cell. Other methods for increasing residence time include: the use of mechanical stirring in conjunction with non-spherical "dimples" or the like strategically located in the equatorial areas of the cell, for example; utilizing directional flow via a perforated nozzle (i.e. showerhead) or the like at the inlet port; and otherwise forcing the fluid to follow a circuitous path inside the cell, by using a randomly bent tube, for example the tube should be made from a UV transparent material, such as quartz or the like. Optimum placement of inlet, outlet, baffles, etc. may be modelled using computational fluid dynamics. It should be noted that any non-uniformities in the cell, such as holes, dimples, baffles, etc. may degrade its optical performance. Thus, successful development of the module and methods of the present invention requires the optimization of the trade-offs between residence time and ideal cell functionality.

The flow cell preferably comprises a control electronic for activating and deactivating the preferably UV-C and/or UV-B light sources. The control unit or control electronic is preferably in communication with the light source or a sensor, wherein the control unit is adapted to analyse the collected data and to output a control signal based on the analysis. For protocol purposes all values will be saved in a data file. The control unit can be realised in hardware and/or in software. The preferably UV-C and/or UV-B light sources, preferably more than 5, especially preferred more than 10 can be disposed about the cell in groups that are activated separately by the control unit. Furthermore, the light sources are preferably operated intermittently or continuously. It was very surprising, that an intermitted operation of the light sources achieves a sufficient disinfection of the sheath fluid, but also increases the durability of the light source. The operation is preferably controlled by the control unit. By dividing the light sources of a module into groups, it is possible to adapt the output of the light sources to parameters of the cell geometry or the sheath fluid. For example, it can be preferred that the preferably UV-C and/or UV-B light sources near the inlet port are operated continuously, whereas the ones near the outlet port are operated intermittently. Furthermore, it can be advantageous when the group of preferably UV-C and/or UV-B light sources at the inlet port are operated intermittently. The durability of the light sources can be efficiently increased by varying the operation modus.

It is further preferred, that the cell comprises at least one sensor. The sensor can be for example a photodetector capable of converting light into either current or voltage. The sensor allows to monitor the functionality of the preferably UV-C and/or UV-B light sources and to adapt the intensity via the control electronic. Furthermore, the intensity of the light sources can be adapted to the transparency of the sheath fluid, ensuring that the power output is sufficient for disinfecting the fluid. One or more sensors can be integrated at various positions within the interior portion of the cell. It is also preferred to include a sensor for measuring the flow rate of the sheath fluid. The output of the preferably UV-C and/or UV-B light sources can be adapted to the flow rate, in that the output is decreased for slow flowing fluids and increased for fast flowing fluids. The adaption of the intensity or output of the preferably UV-C and/or UV-B light sources can be done automatically or manually. The sensor can also be used for controlling groups of preferably UV-C and/or UV-B light sources, by modifying the output power of the light sources to the measured parameters, wherein light sources can be operated continuously or intermittently.

In order to increase the durability of the preferably UV-C and/or UV-B light source and to stabilize the physical properties of the sheath fluid, it is preferred that a cooling device is mounted to the cell, especially to the region of the cell where the light sources are located.

The cooling device can also directly attached to the light source. The cooling device comprises preferably a thermo-electric cooling system (such as a peltier-effect device), cooling fins with a cooling-water, or -air passageway or a ventilation device. Advantageously, a heat exchanger is connected to the cell. The heat exchanger or the cell itself can be provided with surface-enlarging tubular accessories or structures, in particular plates, nets, ribs, protrusions, 2- or 3-dimensional grid structures and/or fins.

Experts are able to empirically determine an optimum arrangement of the surface-enlarging accessories by performing routine tests. The surface-enlarging accessories are preferably made of metal, such as stainless steel, steel, copper or aluminium, as these exhibit high thermal conductivity coefficient and an optimum heat exchange, and ensure thermal conductivity. Experts know that a wide range of different materials can be used. Furthermore, it can be preferred that a fluid is passed through the tubes and/or channels of the cooling device or the heat exchanger and transfers thermal energy away of the cell. For the purposes of the invention, a heat exchanger means in particular an apparatus, which transfers thermal energy from one material flow to another.

In the preferred design of the cell, one or more point preferably UV-C and/or UV-B light sources are disposed within or partially or wholly through one or more ports manufactured through the flow cell, preferably at symmetric positions. The ports housing the light source are preferably light-permissive. It is also preferred, that the preferably UV-C and/or UV-B light sources are arranged outside the interior region of the cell, irradiating the sheath fluid within the interior of the cell. The region of the cell where the light sources are disposed about is preferably made of a light-permissive material. It can also be preferred, that the light sources are arranged within the cell and are kept in direct contact with the sheath fluid. Furthermore, it can be preferred to provide a flow cell with integrated or attachable fibre-optics, through which the light of the light sources is commuting in order to irradiate the sheath fluid.

The flow cell includes at least an inlet port and an outlet port manufactured into it that provides for the flow of the sheath fluid from the inlet port to the outlet port. Preferably, the fluid is not allowed to stagnate in any portion of the interior of the flow cell for an appreciable period of time. It is also preferred that the inlet and outlet ports can be used to clean and disinfect the cell itself if necessary. Therefore, the cell can be unplugged or detached from the flow cytometer and connected to a chemical disinfection solution. However, it is also preferred that the module can be cleaned while still attached to the flow cytometer. The module comprises preferably valves to close the inlet and outlet ports for the sheath fluid while the module is rinsed with a cleaning solution. Furthermore, it can be preferred to pump the sheath fluid into a reservoir or tank, which also comprises the UV light sources. After irradiation, the sheath fluid is pumped from the reservoir or tank into the tubing of the cytometer for further use. In another preferred embodiment, the UV light sources or the module are arranged in the or near the tank of the sheath fluid.

To change the output of the preferably UV-C and/or UV-B light sources, a focussing or diffusing optic can be arranged in front of the light sources. The optic can be easily attached to the light sources and is protected from direct contact with the sheath fluid. The optics can comprise lenses and/or mirrors resulting in a focussing or diffusing of the light of the light source.

The DNA of germs (e.g. viruses, bacteria) will be damaged by the incident UV-C radiation and inactivates so the germ. UV-C radiation at around 265 nm has the highest germicidal potential, which is caused due to the absorption spectrum of DNA. UV-LEDs are commercially available in a broad UV-C spectral range. Therefore, they are preferably be used as a radiation source or light source for the inactivation of microorganisms in the sheath fluid of flow cytometer. Due to the compact design, the performance and free adjustability of the optical output power of the commercial UV-C LEDs it was possible to provide a preferred compact UV-C LED disinfection module, which can be installed effortlessly into the existing flow cytometers. UV-C LEDs have also very fast switch on and off times (certainly less than 100 ns and in some cases even in the ns range) so that also variable intensity modulation schemes can be used for the disinfection.

It is preferred to use the UV-C light source at a pulsed high operation power to improve the efficiency of disinfection. Preferred flow rates of the sheath fluid passing through the tubing of the flow cytometer are in the range of 0.1 to 20 ml/min, preferably 1 to 15 ml/min and especially preferred 2 to 10 ml/min (depending on the size of the sorting cone). However, even higher flow rates can be used for the module. For example, with a flow rate of 3.5 ml/min and a preferred volume of the cell of 8 ml and a preferred exposure time of 150 s, a radiation dose of approximately 40 mWs/cm$^2$ is achieved. This exemplarily calculated dose will be reducing the number of germs in the sheath fluid up to 5 orders of magnitude. The flow through module is preferably located within a short distance to sorting cone, preferably between the nozzle and the sheath fluid tank to prevent a contamination in the hose between the cone and the flow through module. The cells are mixed only within the sorting cone with the sheath fluid and therefore it is no risk of cell damage by the UV irradiation. The exact dimension of the cell (length, diameter) and the number of the UV-C light sources depends on the flow rate of the sheath fluid and the UV-C light source output power, which can however easily determined by the person skilled in the arts.

Surprisingly, by using the module to inactivate the microbiological germs in the sheath fluid of a flow cytometer, disinfection by rinsing with reagents (e.g. Ethanol, NaOH) can be nearly completely abandoned. Exceptions can be long holding times without using the flow cytometer or a strong contamination of the sheath fluid through defects of the flow cytometer. In respect to the clinical use of a flow cytometer the installation of the module achieves additional importance, as a complete replacement of the tubing system is provided but the module could be used preferably as an additional security level. Furthermore, UV-C light sources, preferably LEDs, require only low operating voltages. Therefore the risk for the user through electrical accidents is not given and the control electronics is simplified compared to high voltage mercury vapour lamps. In addition, the lifetime of UV light sources, preferably LEDs, can be significantly higher than that of the conventional mercury vapour lamps so that an exchange of the UV source is not necessary. Typical lifetimes of semiconductor or LEDs in the visible spectral range are in the range of more than 50,000 hours (equivalent to a period of nearly 14 years during a daily operation of 12 hours, 300 days per year). Similar values are also expected for UV LEDs (after a fully development of these components).

Although the invention has been described with respect to specific embodiments and examples, it should be appreciated that other embodiments utilizing the concept of the present invention are possible without departing from the scope of the invention. The present invention is defined by the claimed elements, and any and all modifications, variations, or equivalents that fall within the true spirit and scope of the underlying principles. All described embodiments and advantages in relation to the invented flow cytometer disinfection module are equally valid for the present invention in relation to the invented method for disinfecting. Based on the disclosure of the present invention a person skilled in the art understands how to modify the invention with routine methods in order to solve the problem to be solved by the present invention.

EXAMPLES

The invention is further described by the following examples, which can be applied to various embodiments of the invention. These are not intended to limit the scope of the invention.

Example 1

UV-C and/or UV-B Disinfection-Module Integration in a BD FACS Diva Cell-Sorter

1. Detection of any Existing Contamination in the Cell Sorter
   sample taking (Phosphate Buffered Saline—PBS) from sheath container and PBS stream below the nozzle (each 100 μl)
   receiving the samples in Lysogeny Broth Medium (culture medium for bacteria)
   incubation at 37° C. in a rotating shaker
   after 24 h a clearly contamination was visible in both samples
2. Endotoxin Test at Different Irradiation Dose
   Endotoxin is a component of the outer cell membrane of gram-negative bacteria. It can be detected by a photometric LAL-test.

| sample | light power (mW/light source) | Endotoxin Units (EU/ml) |
| --- | --- | --- |
| PBS container | 0 (positiv control) | 1.01 |
| PBS flow stream* | 0 | >4.95 |
| PBS flow stream* | 0.2 | 2.08 |
| PBS flow stream* | 0.4 | 1.79 |
| PBS flow stream* | 0.6 | 1.55 |
| PBS flow stream* | 0.8 | 1.31 |
| PBS flow stream* | 1 | 2.08 (measurement error) |
| PBS flow stream* | 0 (control) | 1.25 |
| PBS autoclaved | 0 (control) | 3.47 |

*PBS taken below the nozzle

Results (See e.g. FIG. 7):
   a proportional correlation between irradiation dose and endotoxin-level exists
   irradiation dose is insufficient to reduce the endotoxin-level below 0.1 EU/ml
3. UV-C and/or UV-B Module with and without Ethanol Flushing Procedure
   taken 1 ml PBS from flow stream without UV-C and/or UV-B irradiation taken 1 ml PBS from flow stream with UV-C and/or UV-B irradiation (0.2-0.7 mW, instability of LED power!!)

taken 1 ml PBS from flow stream with UV-C and/or UV-B irradiation (0.5 mW)

tube washing for 5 min (tubing between UV-C and/or UV-B module and nozzle) with Ethanol and 1 h with PBS taken 1 ml PBS from flow stream with UV-C and/or UV-B irradiation (0.6 mW)

taken positive-control from sheath container incubation at 37° C. in a rotating shaker Results:

| dose (mW/light source) | 0 | 16 h | 18 h | 19 h | 22 h | 25 h | 40 h |
|---|---|---|---|---|---|---|---|
| PBS flow stream (without UV-C and/or UV-B, positive-control) | − | − | + | + | + | + | + |
| PBS flow stream (0.2-0.7) | − | − | − | − | + | + | + |
| PBS-flow stream (0.5) | − | − | − | − | − | + | + |
| PBS-flow stream (0.6 after Ethanol washing) | − | − | − | − | − | − | + |
| PBS-sheath container (positiv-control) | − | + | + | + | + | + | + |
| negative control (LB-Medium only) | − | − | − | − | − | − | − |

+ LB-medium turbidity → bacteria contamination
− No LB-medium turbidity → bacteria contamination 4. Repetition of EtOH Flushing Experiment tube washing between Nozzle and UV-C and/or UV-B module taken 1 ml PBS from flow stream with UV-C and/or UV-B irradiation (0.6 mW)

taken 1 ml PBS from flow stream without UV-C and/or UV-B irradiation incubation at 37° C. in a rotating shaker

| dose (mW/light source) | 0 | 4 h | 15 h | 24 h | 29 h | 32 h | 5 d |
|---|---|---|---|---|---|---|---|
| PBS-flow stream (0.6) | − | − | − | − | − | − | − |
| PBS-flow stream (UV-C and/or UV-B module off) | − | − | − | + | + | + | + |
| PBS-sheath fluid container (positive control) | − | − | + | + | + | + | + |
| negative control (LB-medium only) | − | − | − | − | − | − | − |

5. Test on LB-Agar Plates (Quantification of Colony Forming Units/ml-CFU/ml) and LB-Medium samples taken at 0.8 mW, 0.6 mW, 0.2 mW and 0 mW (with/without EtOH-washing)

samples were allocated on LB-medium and Agar no contamination on LB Agar detectable after 9 days a contamination on LB medium was visible sample 0.2 mW and 0.6 mW, after 2 days a contamination on LB Medium was detected a) Test on LB-Agar, without EtOH Flushing

| dose (mW/light source) | 0 | 23 h | CFU/ml |
|---|---|---|---|
| PBS-flow stream (0.8) | − | + | >1770 |
| PBS-flow stream (0.6) | − | + | >2400 |
| PBS-flow stream (0.2) | − | + | >2200 |
| PBS-flow stream (UV off) | − | + | >2000 |
| negativ control ("empty" Agar-plate) | − | − | — |
| positiv control (PBS, taken from sheath-container) | − | +++ | 1 * 10⁵ |

Results:

1*10⁵ CFU/ml (PBS Sheath container) was reduced to 1770 CFU/ml→reduction of 1.7 log levels b) Test on LB-Agar, with EtOH Flushing

| dose (mW/light source) | 0 h | 23 h | 28 h | 45 h | 46 h | 70 h | CFU/ml |
|---|---|---|---|---|---|---|---|
| PBS-flow stream (0.8) | − | − | − | − | − | − | − |
| PBS-flow stream (0.6) | − | − | − | − | − | − | − |
| PBS-flow stream (0.2) | − | − | − | − | − | − | − |
| PBS-flow stream (without UV-C and/or UV-B) | − | − | − | − | + | + | >2100 |
| Negative control ("empty" Agar-plate) | − | − | − | − | − | − | − |
| positive control | − | +++ | +++ | +++ | +++ | +++ | 1*10⁵ |

Results:

no contaminations in samples after EtOH flushing and UV-C irradiation c) Test on LB-Medium, without EtOH Flushing

| dose (mW/light source) | 0 h | 5 h | 21 h | 24 h | 29 h | 45 h | 50 h | 52 h | 68 h | 8 d |
|---|---|---|---|---|---|---|---|---|---|---|
| PBS-flow stream (0.8) | − | − | − | + | + | + | + | + | + | + |
| PBS-flow stream (0.6) | − | − | − | + | + | + | + | + | + | + |
| PBS-flow stream (0.2) | − | − | − | + | + | + | + | + | + | + |
| PBS-flow stream (without UV) | − | − | − | + | + | + | + | + | + | + |
| Negative control (LB-medium only) | − | − | − | − | − | − | − | − | − | − |
| positive control (PBS sheath-fluid container) | − | − | + | + | + | + | + | + | + | + | d) Test on LB Medium, with EtOH-Flushing

| Dose (mW/light source) | 0 h | 5 h | 21 h | 24 h | 29 h | 45 h | 50 h | 52 h | 68 h | 8 d |
|---|---|---|---|---|---|---|---|---|---|---|
| PBS-flow stream (0.8) | − | − | − | − | − | − | − | − | − | + |
| PBS-flow stream (0.6) | − | − | − | − | − | + | + | + | + | + |
| PBS-flow stream (0.2) | − | − | − | − | − | + | + | + | + | + |
| PBS-flow stream (without UV) | − | − | − | − | − | + | + | + | + | + |

-continued

| Dose (mW/light source) | 0 h | 5 h | 21 h | 24 h | 29 h | 45 h | 50 h | 52 h | 68 h | 8 d |
|---|---|---|---|---|---|---|---|---|---|---|
| negative control (LB-Medium only) | − | − | − | − | − | − | − | − | − | − |
| positive control (PBS sheath-fluid container) | − | − | + | + | + | + | + | + | + | + |

6. Cell Culture Test
  EtOH tube flushing between UV module and nozzle
  running for 15 min with PBS
  cell-sorter setup (Laser calibration and DropDelay)
  sample line flushing with EtOH
  sort of XMG 1.2 hybridoma cells (B-cells and Myelom-cells) each sample $2\times10^5$ cells in Falcon tubes w/o P/S, gate on SSC and FSC, at 0.28 V and 0 V light source (e.g. LED) voltage
  sorting time: 21 min
  sorted cells were taken into cell culture as well as allocated on LB-Agar plates and LB-medium
Results:
  all cell cultures were contaminated after 1 day
  no contamination on LB-Agar sample (0.28 V), PBS only
  contamination of LB-Agar sample (0 V) after 24 h (1000 CFU/ml), PBS only
  positive control: PBS taken from sheath-fluid container (after 24 h, 400 CFU/ml)
  contamination of LB-medium samples (0.28 V and 0 V) after 24 h
7. Sample Line Contamination Test
  sample line flushing with EtOH
  PBS taken below the nozzle (0.29V UV-C voltage) without sample line fluid
  PBS taken below the nozzle (0.29V UV-C voltage) with sample line fluid (sterilized water)
  samples were incubated at 37° C. in LB medium
  no contamination after 3 days
8. Polytetrafluorethylene (Teflon) UV-C and/or UV-B Module:
  a module composed of Polytetrafluorethlyene was used, number of light sources as before
  cell sorter setting: 100 μm nozzle at 10 psi, which results in a flow rate of 4.8 ml/min
  chemical decontamination with Bleach (BD FACSClean) for 15 min
  samples taken below the nozzle, sheath-fluid container and sheath-filter
  samples taken at max. dose
  samples were allocated on Agar plates
Result:
  no contamination on LB Agar detectable after 24 h
Next Experiment:
  after 6 days samples were taken at sheath-container, sheath-filter and below the nozzle
  samples were allocated on Agar plates
  a contamination of $1.4*10^5$ CFU/ml was detected in sheath-filter
  no contamination below the nozzle
Result:
  The UV-C and/or UV-B (Teflon) module is able to reduce the germ number for about 4.5 log units.
9. Decontamination Test at Different UV-C and/or UV-B Dose
  contamination of $1.35*10^5$ CFU/ml at sheath-filter was detected
  Light output of the light source (e.g. of LEDs) is calculated by the voltage at the module as follows:
  $U(V)=0.2054+0.11309*P(mW)$
  samples taken below the nozzle at:
    1. 0.24V/10.4 mW
    2. 0.23V/7.4 mW
    3. 0.22V/4.4 mW
    4. 0.21V/1.4 mW
    5. 0.20V/0.0 mW
    6. 0.19V/0.0 mW
    7. 0.00V/0.0 mW->5170 CFU/ml contamination
Result:
  samples 1-6 were negative, no contamination
10. Decontamination Test at Different UV-C and/or UV-B Dose (Percentage Units)
  samples taken from the sheath-container and below the nozzle at:
    1. 100% dose
    2. 75% dose
    3. 50% dose
    4. 25% dose
    5. 0% dose
  samples were allocated on Agar plates
Results:

| Dose/% | Contamination after 24 h/CFU/ml |
|---|---|
| 100 | 0 |
| 75 | 0 |
| 50 | 10 |
| 25 | 520 |
| 0 | 950 |

Figure 8:
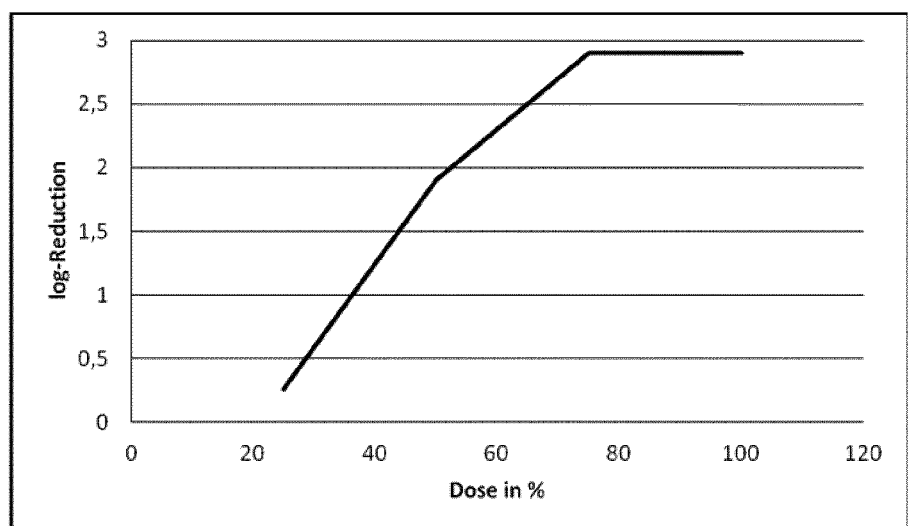

See also FIG. 8.

11. Summary
  The preferred embodiment of the module was able to achieve a 5 log reduction of microbiological contamination (CFU/mml or Endotoxin) after UV-C and/or UV-B irradiation of the sheath fluid by light sources. Contamination of the sheath fluid tubing between UV-C and/or UV-B module and nozzle results in a reduction of the module-efficiency for about 3 log units. The same surprising results have been achieved using other UV-C and/or UV-B light sources in the module.

FIGURES

Figure 1B:
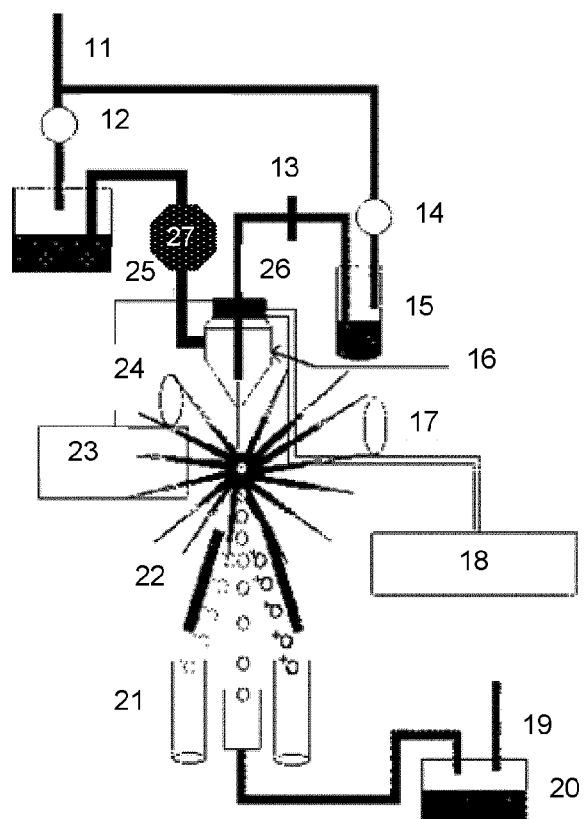

The invention is further described by the following figures and examples. These are not intended to limit the scope of the invention.
  FIG. 1A, B Module integrated into a flow cytometer
  FIG. 2A, B Preferred designs of a module
  FIG. 3 Another preferred design of a module
  FIG. 4A, B Arrangement of UV-C and/or UV-B LEDs and sensors within a flow cell
  FIG. 5 Distribution of power output
  FIG. 6A, B Preferred embodiment of a flow cell
  FIG. 7 Results of an experiment
  FIG. 8 Results of an experiment
  FIG. 1A, B show a schematic sketch of a preferred embodiment of the disinfection module integrated in a flow cytometer. The module 27 is preferably integrated between a sheath fluid tank 28 and a nozzle 16 of the flow cytometer, wherein sheath fluid is mixed with a sample 15. Waste fluid is transported into the waste tank 20. Further parts of the cytometer are air pressure 11, sheath pressure 12, valves 13, sample differential 14, forward scatter collection lenses 17, transducer frequency generator 18, vacuum line 19, cell collection 21, deflection plates 22, sort logic controller 23, side scatter and fluorescence collection lenses 24, charging electrode 25 and transducer 26. The module 27 can be integrated in any flow cytometer, and the one shown in FIG. 1B is just an example and can of course built in any other way. Respectively, the parts of the cytometer are also listed exemplarily. The module 27 has preferably a central body (or flow cell 7) with a diameter of especially 9.5 cm and a height of 2 cm. It can be made of metal, glass or polymer. In the case of a metal, preferably aluminium, the aluminium block is a spiralshaped channel. In addition, holes with conventional connections were integrated for the inflow 31 and outflow 32 of the liquid (where conventional laboratory tubes can be connected to). The course of the channel is designed in such a way that it passes the UV-C and/or UV-B light source 8. The number of UV-C and/or UV-B light sources 8 can vary in dependence to different applications. The spiral shape is a preferred embodiment and has a long exposure time of the liquid and simultaneously realises a compact design of the entire module 27. Since aluminium is a good UV reflector (R~90%) a part of the UV light can be recycled which increases the efficiency of UV disinfection. Furthermore, a cell 7 made of polymer is also preferred. The UV reflective surface also improves the uniformity of illumination in the channel. It can be preferred to create a cell 7 made from a chemically inert UV reflective material. This could be for example a polymer material like ePTFE™ ("expanded" Polytetrafluorethylen) or Spectralon™ (PTFE, Polytetrafluorethylen), which have a diffuse reflectivity of 99% and over 95% in the UV-B and UV-C spectral region, respectively. Possibly, the PTFE material could also be used as a thin UV reflective passivation layer of to the channel surface. Also polymers like PEEK (Polyether ether ketone) can be used. Other preferred UV reflective thin film coatings are MgO (R>80% in the UVB/C range), ZrO2 (R~78% in the UVB/C range) or BaSO4. It is further preferred to passivate the last coating with a SiO2 layer or some similar think, as these materials may react with these solutions.

The bottom of the flow through module 27 is preferably covered with a 2 mm thick UV transparent or light-permissive-material 34, such as synthetic quartz glass (diameter 8 cm). Quartz glass has from all practicable usable materials in the UV-C and/or UV-B spectral range the highest transmission (over 90%). The light-permissive material 34 (e.g. quartz glass) is preferably inserted 2 mm into the flow cell 7 body and attached by a metal ring, which is pressed by screws to the metal body. A seal between glass and aluminium body is especially made of silicone and an O-ring. In principle it is also possible to integrate the UV-C light source 8 directly in the body of the module 27, especially the wall of the interior region 9 of the cell 7. It is also preferred to use a UV transparent polymer, such as PDMS (Polydimethylsiloxan) as a light-permissive material 34. This UV transparent polymer could also be used as a light guider to distribute the UV-light uniformly over the entire channel system.

In a preferred embodiment, the light sources 8 are oriented within an array, wherein the array is located in a groove or the groove is located around the array. Thus, for each measurement the same distance and the same orientation of the flow through module 27 is guaranteed, which is very advantageous for the reproducibility of the disinfection effect.

The used UV-C and/or UV-B light sources 8, especially the UV-C LEDs have an emission wavelength of around 269 nm or 282 nm and a preferred small full width of half maximum of 10 nm to 11 nm. The emission spectra of the UV-C light sources 8 have an ideal overlap with the absorption spectrum of the DNA of the microorganisms. The optimal emission wavelength is given by the potential output power and efficiency of the UV-C light source 8 at a corresponding wavelength and the optimum wavelength for germicidal effectiveness. The maximum of the germicidal effects of UV radiation is approximately at 265 nm and decreases as shorter and longer wavelengths. The wavelength range in which the germicidal effect is greater than 50% is between 243 nm and 287 nm. More than 20% are possible in the wavelength range between 226 nm and 304 nm. Group III—nitride based light sources are preferred, as they can be realized in the entire spectral range, in that it is also possible to manufacture a disinfection module 27 with UV-C light sources 8 with longer or shorter wavelength.

UV-C and/or UV-B light sources 8 are preferably used with a constant power supply. Thereby the current and accordingly to that the output power is infinitely adjustable to its maximum value. Thus, the total output power of the UV light sources module 27 can be adapted to the flow rate of the sheath fluid. The output power of UV light sources 8 is preferably measured with a sensor 33, for example a silicon photodiode. In a preferred embodiment, the output power of the UV light sources 8 is measured with an external sensor 33 (e.g. photodiode) and then manually adjusted. In a preferred version of the disinfection module 27 this photodiode is integrated into the flow cell 7, especially the channel in the interior region 9, which allows an active feedback during the disinfection process. Thus, the current for the UV light sources 8 are adjusted automatically if degradation by decreasing of the light output of UV light sources 8 takes place. Thus, it is possible to guarantee the same output power at any time, which is very advantageous for the reproducibility of the disinfection performance. The arrangement of the photodiode in the interior region 9 of the cell 7 can be made in such way that the transmission of the sheath fluid is taken into account and so in highly UV absorbing liquids more UV light output power would be automatically used in order to achieve the required disinfection performance.

A flow through module 27 with more than 2, preferably more than 10, for example 35 UV light sources 8, especially UV-C LEDs (wavelength=282 nm) could be realised. In this preferred module all drive and measurement electronics was implemented in one unit.

The control and measurement electronics for the UV light sources 8 and the power supply is preferably integrated in the same unit. The light output power of the light sources 8, especially the LEDs can be varied in a range between 0 and 1 mW per LED. The emission power of the light sources 8, especially the LEDs is measured with a reference light source 8 or LED (operating time is identical to the LED array) and another sensor 33 (for example a UV sensitive photodiode). Preferably a silicon photodiode can be used, but also UV photodiodes made from other semiconductor materials can be used, e.g. GaP, InGaP, SiC, AlGaN, and GaN. The UV photodiodes include preferably pin-diodes, Schottky contact diodes, and metal-semiconductor metal photodiodes. They are protected against any light radiation so that the measurements cannot be falsified and a use of the module 27 under any light conditions is possible. The photodiode is preferably connected to an integrated voltmeter or ampere-meter. Therefore the light output power of the LED arrays (which is proportional to voltage) can be easily determined after a calibration of the UV disinfection module 27.

The light sources 8 in the disinfection module 27 are preferably operated at the same voltage and same current. A continuous variation of the light output power is preferably realised by a change of the duty cycle (that means the ratio of the pulse duration to pulse period). The setting of the various light output powers is possible manually or by connecting the module to a PC. It can also be preferred to use software to run certain routines e.g. the lights turn off automatically after a specified time. Of course it is also preferred to operate the light sources 8 in continuous wave operation and adjust the performance of the applied voltage or the operating current. In some case it could also be advantageous to use a combination of both regulation methods.

Figure 2:
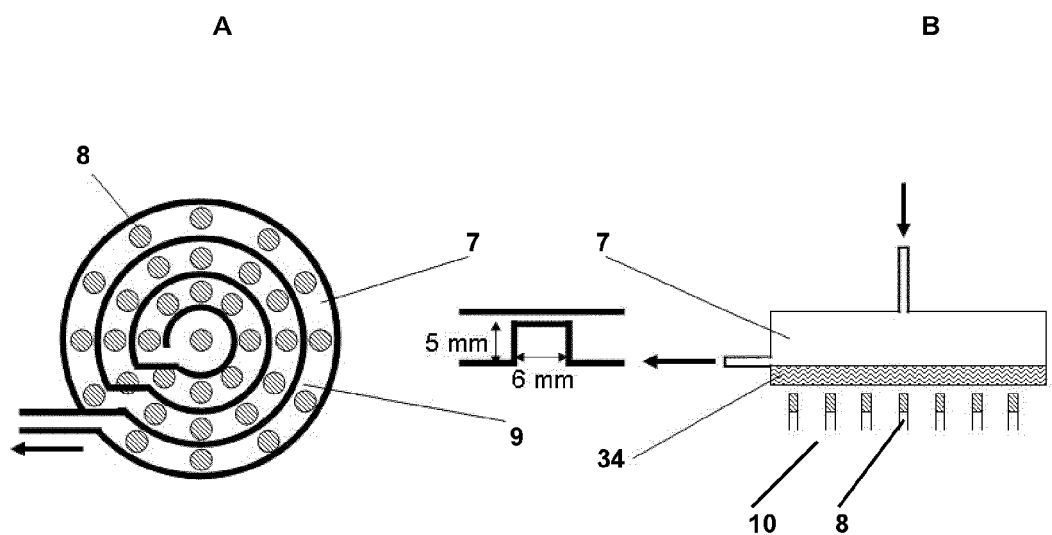

In FIG. 2A, B preferred designs of a module are shown. The module can be made in a spiral shape (A) or any other shape. FIG. 2B shows FIG. 2A from a different angle. The UV light sources 8 can be arranged within a light-permissive housing within the interior portion 9 of the cell 7 or around the outer portion 10 of the cell 7. The preferred module 27 consists of an aluminium plate were 35 UV-C light sources 8, for example LEDs are integrated (with a wavelength of 282 nm). The design of the resulting LED array is preferably constructed concentrically. Thus, the LEDs are especially on 3 concentric circles with a diameter of 1.8 cm (equipped with 6 LEDs), 3.5 cm (equipped with 12 LEDs) and 5.2 cm (equipped with 16 LEDs). With the preferred embodiment, an irradiation of the flow through module can take place. The light sources 8 can be arranged in an outer region 10 of the cell 7 or within an interior region 9. If the light sources 8 are assembled in an outer region 10, the light sources 8 preferably emit UV light through a light-permissive channel or part of the channel of the cell, to irradiate the sheath fluid flowing through the interior region 9 of the cell 7. The cell 7 can be made of metal, polymer or glass. If the light sources 8 are arranged in the outer portion of the cell 7, the light sources 7 emit light through a light-permissive material 34. The light-permissive material 34 can be a part of the cell 7 or the cell 7 can be wholly made of the material.

Figure 3:
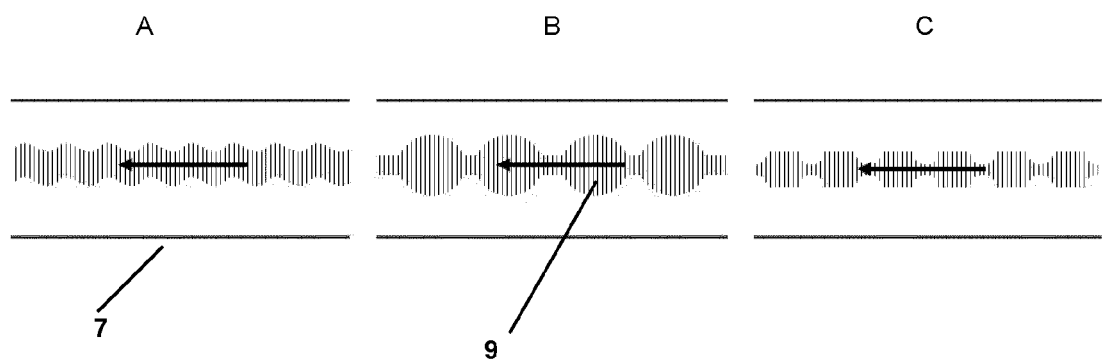

FIG. 3 shows preferred embodiments of the cell 7. To create turbulence within the flowing fluid in order to ensure a uniform irradiation, the cell 7 can be comprise various designs or mechanical baffles. A preferred design of the cell provides a structuring of channels or interior regions 9 of the cell 7. The periodic rejuvenation or wave-shaped guide of the channel diameter leads to a local increase in the flow speed (indicated by the arrow) and so in a subsequent turbulence of the water flow.

Figure 4:
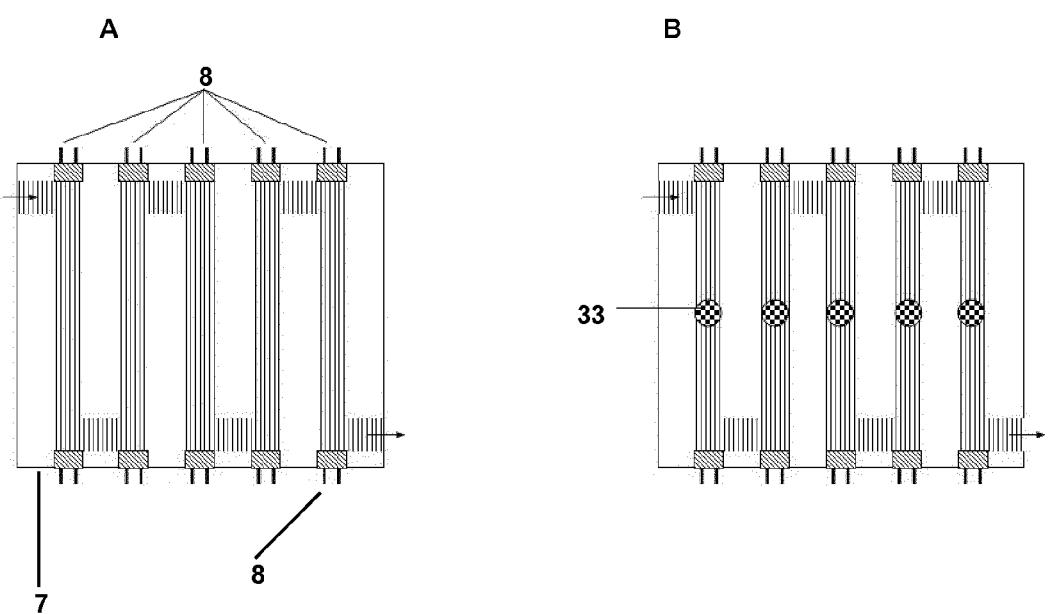

FIG. 4A, B shows arrangement of UV-C and/or UV-B light sources, especially LEDs and sensors within a flow cell. The UV light sources 8, for example UV-C and/or UV-B LEDs can be arranged outside the cell 7 and irradiating the sheath fluid flowing through the cell 7 (indicated by the arrows). Furthermore, sensors 33 (e.g. photodetectors) can be arranged in the cell 7 to measure the light intensity of the light sources 8, ensuring optimal contribution of the light and functionality of the light sources. A preferred alternative for the coupling of the UV-C and/or UV-B light from the top or the bottom would be the coupling of the UV light sources along the canal. This could be realised with a lateral mounting of the light sources 8. The channel walls of the cell 7 are preferably made of an UV reflecting material so that the UV light is distributed as evenly as possible in the channels. That would reduce the number of light sources 8, which reduces the costs and facilitate the control. In addition, it is preferred to use one or more UV photodiodes (UV PD) to install perpendicular to the direction of liquid flow in each channel centre (between the two UV light sources 8) in order to measure the UV light output power in the channel. The channel preferably runs through the interior region of the cell 7, wherein the sheath fluid is passing through the channel. The information generated by the photodiodes could be used for an active feedback to regulate the UV light source output power. That could be advantageous if the UV light source 8 output power decreases by a degradation of the UV light source or by a change of the transmission of the liquid to realise the right UV disinfection dose. Another preferred embodiment would be a Peltier cooling element on the channel surface or channel bottom, in order to prevent a possible heating of the liquid by the light sources 8. Or it can generally provide to improve the temperature stability of the liquid.

Figure 5:
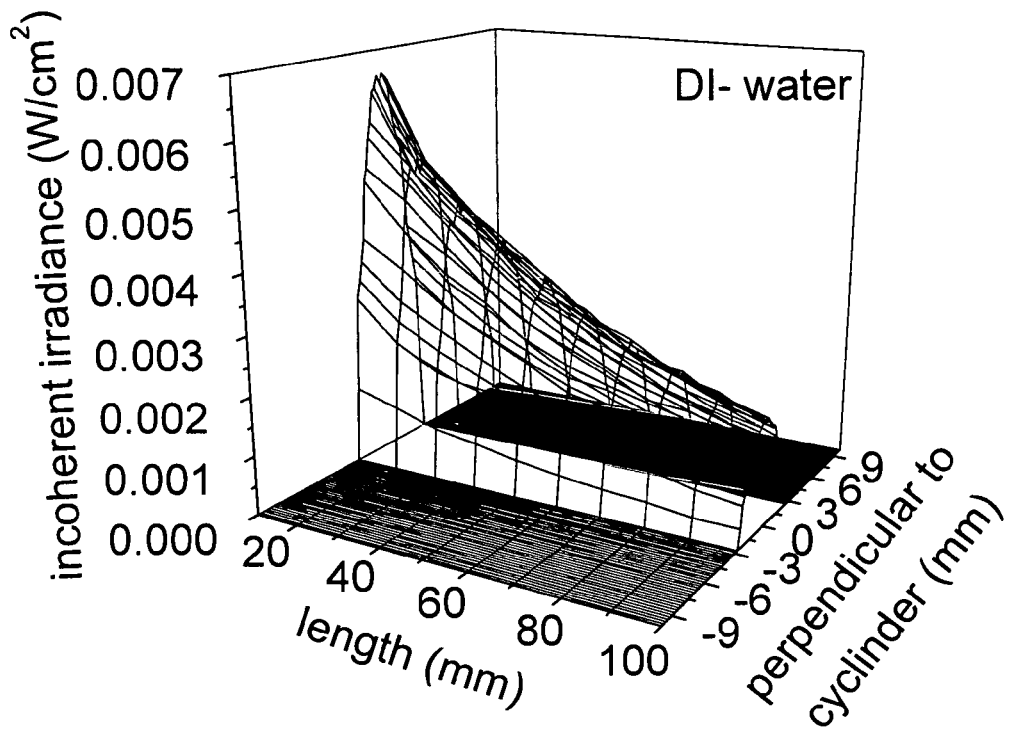
Figure 5:
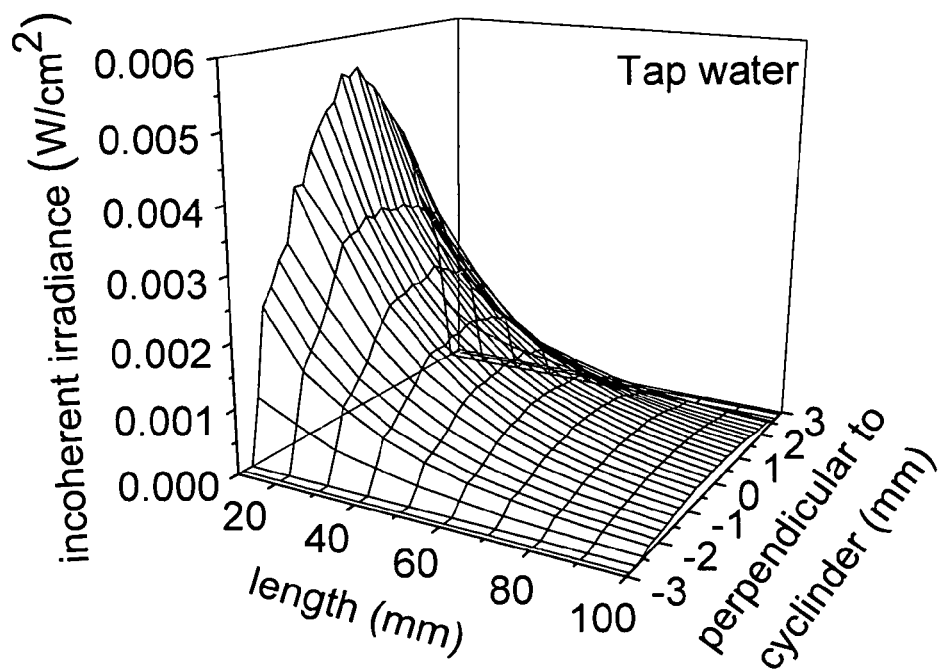

FIG. 5 shows the distribution of the LED power output. Distribution of light output power along a cylindrical channel with UV-reflecting walls (R~90%). The diameter of the channel is in a preferred embodiment 5 mm and the length (length) 100 mm. The UV light from the LED (light output power assumed as 1 mW at 280 nm) is preferably coupled centered from the left side (length=0 mm) coaxially in the channel. The left curve shows the distribution of light output power with deionised (DI) water (transmission=94% per cm) and the right curve shows the distribution for tap water (transmission=78% per cm). It can be seen that the light output decrease along the canal. The light output power is also unevenly distributed perpendicular to the flow direction. The light output power is the highest in the middle of the channel and decreases in direction to the walls. For a uniform dose rate the liquid should be mixed during the disinfection. Alternatively or additionally the maximum LED performance should be choose in such way that the minimum disinfection dose of 40 mWs/cm2 can be realised on the walls of the disinfection module. Since the flow velocity decrease also radial symmetry from the centre to the walls there is partly a compensation of the lower light output power on the walls because the interaction time increases with decreasing flow rate (crucial is the light dose=power*time).

Figure 6:
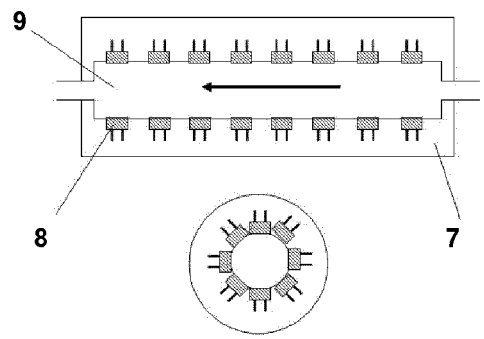
Figure 6:
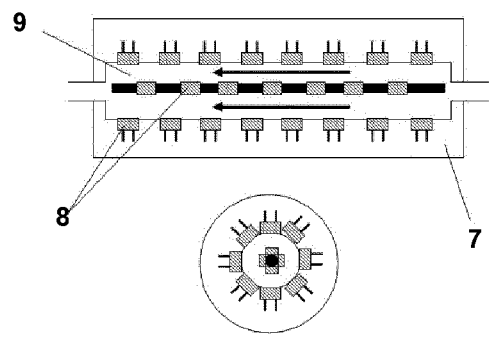

In FIG. 6A, B a preferred embodiment of a flow cell is shown. The cell 7 can be designed in various ways. The UV-C and/or UV-B light sources 8 can be arranged in the interior region 9 of the flow cell 7, wherein the cell 7 can be linear, spiral, U-shaped, cylindrical, rectangular, helical or ellipsoid shaped. Further designs of the cell 7 are also preferred.

Figure 7:
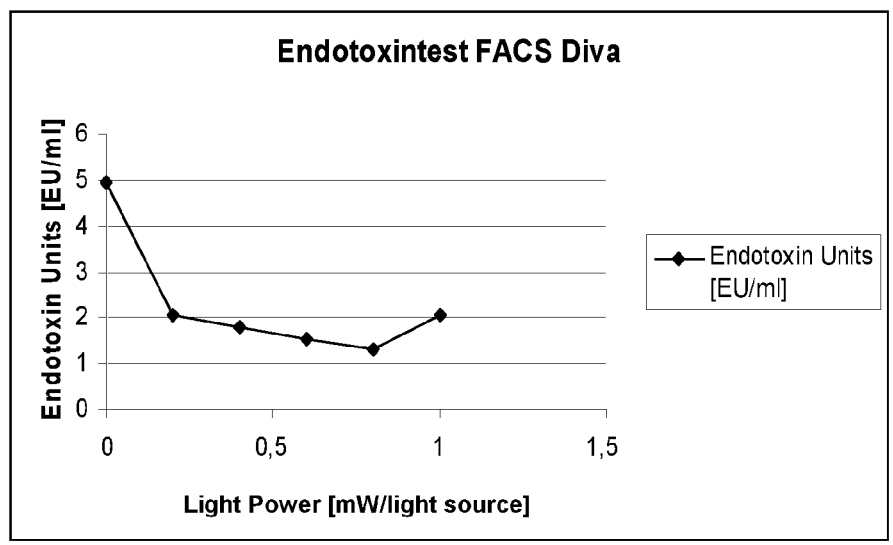

FIG. 7 shows a result of test run with a preferred module (Example 2). The microbiological contamination within the sheath fluid decreases with increased power output of the light sources. In the experiment various UV light sources have been used, but only the result of the UV LEDs is shown.

FIG. 8 shows another result of an experiment (Example 10), indicating that an increased dose results in an increased reduction.

LEGEND FOR FIGURES

7 Flow Cell
8 Light Source
9 Interior Region
10 Outer Region
11 Air Pressure
12 Sheath Pressure
13 Valve
14 Sample Differential 15 Sample
16 Nozzle
17 Forward Scatter Collection Lens
18 Transducer Frequency Generator
19 Vacuum Line
20 Waste Tank
21 Cell Collection
22 Deflection Plates
23 Sort Logic Controller
24 Side Scatter and Fluorescence Collection Lens
25 Charging Electrode
26 Transducer
27 UV-C and/or UV-B module
28 Sheath Fluid Container/Tank
29 Sheath Fluid Tubing
30 Cytometer
31 Inlet Ports
32 Outlet Ports
33 Sensor
34 Light-Permissive Material

The invention claimed is:

1. An assembly comprising:
   (a) a flow cytometer, and
   (b) a flow cytometer disinfection module connected to the flow cytometer, comprising
       (i) a flow cell, and
       (ii) at least one ultraviolet, electromagnetic radiation subtype C (UV-C) and/or ultraviolet, electromagnetic radiation subtype B (UV-B) light source, wherein the at least one UV-C and/or UV-B light source is disposed about the flow cell and irradiates a sheath fluid of the flow cytometer passing through the flow cell, and wherein the light source is assembled within a wall of an interior region of the flow cell in a light-permissive housing and/or outside of the interior region of the flow cell irradiating the sheath fluid through a light-permissive material,
   wherein the module is connected to sheath fluid tubing and installed between a nozzle and a sheath fluid tank of the flow cytometer.

2. The assembly according to claim 1, wherein the flow cell is linear, spiral, U-shaped, cylindrical, rectangular, helical or ellipsoid shaped.

3. The assembly according to claim 1, wherein the light source is a light-emitting diode (LED) or a semiconductor.

4. The assembly according to claim 1, wherein the flow cell is made of polymer, glass and/or metal.

5. The assembly according to claim 1, wherein the flow cell is made out of polytetrafluoroethylene (PTFE).

6. The assembly according to claim 1, wherein the flow cell comprises inlet and outlets ports.

7. The assembly according to claim 1, wherein the flow cell comprises mechanical baffles and/or stirring mechanisms disposed within the cell.

8. The assembly according to claim 1, wherein the flow cell comprises an interior surface for reflecting the radiation.

9. The assembly according to claim 1, wherein the flow cell comprises at least one sensor.

10. The assembly according to claim 1, wherein a cooling device is mounted to the flow cell.

11. The assembly according to claim 1, wherein the light source is assembled within a wall of an interior region of the flow cell.

12. The assembly according to claim 1, wherein the light source is assembled in a light-permissive housing within a wall of an interior region of the flow cell.

13. The assembly according to claim 1, wherein the light source is arranged outside of the interior region of the flow cell irradiating the sheath fluid through a light-permissive material.

14. The assembly according to claim 1, wherein the UV-C and/or UV-B LED emits light with 240 nm-290 nm.

15. The assembly according to claim 1, wherein the LED is gallium nitride based.

16. The assembly according to claim 1, wherein the flow cell comprises an electronic control for activating and deactivating the light source.

17. The assembly according to claim 1, wherein more than 5 UV-C and/or UV-B light sources are disposed within the flow cell.

18. The assembly according to claim 17, wherein more than 10 UV-C and/or UV-B light sources are disposed within the flow cell.

19. The assembly according to claim 1, wherein the light sources are divided into groups, which are activated separately by the electronic control.

20. The assembly according to claim 1, wherein light sources are operated intermittently or continuously.

21. The assembly according to claim 1, wherein a focusing or diffusing optic is arranged in front of the light source.

22. The assembly according to claim 1, wherein the light sources are operated with an accumulator or batteries.

23. A method for disinfecting a sheath fluid in a flow cytometer, said method comprising the steps of:
    obtaining an assembly according to claim 1; and
    irradiating the sheath fluid passing through the flow cell with the at least one UV-C and/or UV-B light source.

* * * * *